United States Patent [19]

Kranz et al.

[11] Patent Number: 4,536,353

[45] Date of Patent: Aug. 20, 1985

[54] PROCESS FOR PREPARING α-KETONITRILES

[75] Inventors: Eckart Kranz, Wuppertal; Kurt Findeisen, Odenthal, both of Fed. Rep. of Germany

[73] Assignee: Bayer Aktiengesellschaft, Leverkusen, Fed. Rep. of Germany

[21] Appl. No.: 667,524

[22] Filed: Nov. 2, 1984

[30] Foreign Application Priority Data

Nov. 11, 1983 [DE] Fed. Rep. of Germany ....... 3340933

[51] Int. Cl.³ ............................................ C07C 120/00
[52] U.S. Cl. ................................ 260/545 R; 556/416; 564/158
[58] Field of Search .................................... 260/545 R

[56] References Cited

U.S. PATENT DOCUMENTS 4,360,479 11/1982 Findeisen et al. .............. 260/545 R Primary Examiner—Dolph H. Torrence
Attorney, Agent, or Firm—Sprung, Horn, Kramer & Woods

[57] ABSTRACT

A process for preparing an α-ketonitrile of the formula

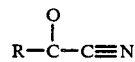

in which R is optionally substituted aryl, comprising reacting a cyanohydrin of the formula

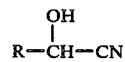

with sulphuryl chloride or thionyl chloride.

8 Claims, No Drawings

PROCESS FOR PREPARING α-KETONITRILES

The present invention relates to a chemically distinctive process for preparing α-ketonitriles.

It is known to produce α-ketonitriles from carboxylic acid halides by reacting the latter at temperatures of 100° C. to 300° C. in the presence of catalytic amounts of copper(I) cyanide, copper(II) cyanide, zinc cyanide or their complexes with alkali metal cyanides or hydrogen cyanide (compare for example German Published Specification DE-AS No. 2,614,242).

It is also known that the reaction of cyanohydrins with thionyl chloride is accompanied by substitution of the hydroxyl grouping (compare in this context J. Chem. Soc. 1945, 352; Japanese Patent Specification No. 57-123,175; Derwent Abstract 69,071 R of Soviet Patent Specification 255,294 and Derwent Abstract 27,727 S of Soviet Patent Specification 268,438). This substitution likewise occurs in the reaction of alcohols with sulphuryl chloride (compare in this context Houben-Weyl-Müller, Volume IV/2, page 466, Thieme Verlag Stuttgart).

It has now been found, surprisingly, that α-ketonitriles of the formula (I)

in which R represents optionally substituted aryl, are obtained when cyanohydrins of the formula (II)

in which R has the abovementioned meaning, are reacted at temperatures between 15° C. and 30° C. with sulphuryl chloride or thionyl chloride in the presence or absence of chlorinated hydrocarbons.

It is surprisingly possible to oxidize the cyanohydrins by means of the process according to the invention. This is all the more surprising since, according to the state of the art, the reaction of cyanohydrins with sulphuryl chloride or thionyl chloride should have lead to the formation of either α-chlorosulphonylnitriles or α-chlorosulphinylnitriles or α-chloronitriles to a considerable extent (compare in this context U.S. Pat. No. 3,470,493; Derwent Abstract 69,071 R of Soviet Patent Specification No. 255,294 and Derwent Abstract 27,727 S of Soviet Patent Specification 268,438).

The process according to the invention is preferably used for preparing the following α-ketonitriles: 2-chloro-, 4-chloro-, 3,4-dichloro-, 3,5-dichloro-, 3,4,5-trichloro-, 2,6-dichloro- and 2,4-dichlorobenzoyl cyanide and benzoyl cyanide.

The process according to the invention is used particularly preferably for the following compounds of the formula (I): 2-chloro-, 4-chloro-, 3,4-dichloro-, 3,5-dichloro- and 3,4,5-trichloro-benzoyl cyanide.

If the starting materials are 3,4-dichloro-α-hydroxybenzylnitrile and sulphuryl chloride, the course of the reaction can be represented by the following reaction equation (a):

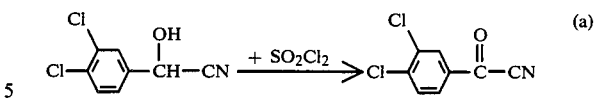

If 4-chloro-α-hydroxybenzylnitrile and thionyl chloride are used as the starting materials, the course of the reaction can be represented by the following reaction equation (b):

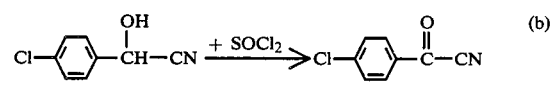

The cyanohydrins used as starting materials are defined in general terms by the formula (II), in which R preferably represents aryl—such as in particular phenyl—which is optionally monosubstituted to trisubstituted by $C_1$-$C_4$-alkyl, $C_1$-$C_4$-alkoxy, nitro and/or halogen, such as fluorine, chlorine or bromine.

Preferred examples of cyanohydrins of the formula (II) are in particular phenyl-, 2-chlorophenyl-, 4-chlorophenyl-, 3,4-dichlorophenyl-, 3,5-dichlorophenyl-, 2,4-dichlorophenyl-, 2,4-dichlorophenyl-, 4-methoxyphenyl- and 3,4,5-trichlorophenyl-cyanohydroxymethane.

The cyanohydrins of the formula (II) are commonly known compounds of organic chemistry.

Possible diluents for carrying out the process according to the invention are preferably halogenated hydrocarbons, such as chloroform, methylene chloride, methyl chloride and carbn tetrachloride. In principle, however, it is also possible to carry out the reaction according to the invention in the absence of diluents, other than excess reagent.

The reaction is generally carried out at temperatures between 15° C. and 30° C., preferably at room temperature.

The reaction is generally carried out under atmospheric pressure.

In carrying out the process according to the invention, 1.0 to 10.0 moles, preferably 1.0 to 2.5 moles, of sulphuryl chloride or thionyl chloride are generally used per mole of cyanohydrin of the formula (II).

The reaction product is worked up by customary methods. The purity of the compounds is determined by gas chromatography. They are characterized by GC-MS data and/or the melting point.

The α-ketonitriles readily producible by the process can be used, for example, for synthesizing insecticides. For instance, they can be used to prepare substituted hydroxymalondiamides, which are compounds of high insecticidal potency, according to, for example, the following equations:

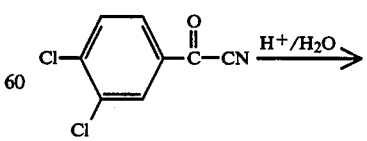

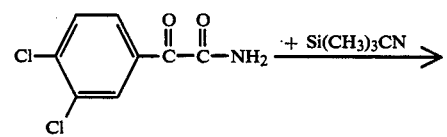

-continued

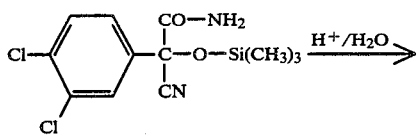

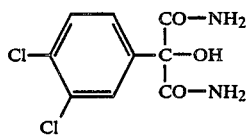

The substituted hydroxymalondiamides and their use as insecticides are known (compare German Published Specification DE-OS No. 3,140,275).

PREPARATION EXAMPLES
EXAMPLE 1a

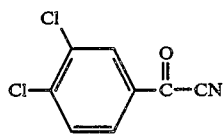

20.2 g (0.1 mole) of cyano-(3,4-dichlorophenyl)-(hydroxy)-methane are dissolved in 100 ml of methylene chloride. 13.1 g (0.11 mole) of sulphuryl chloride are then added dropwise at room temperature, and the mixture is stirred at said temperature for 16 hours. The small amount of precipitate is filtered off with suction, and the solution is freed of the solvent and excess sulphuryl chloride.

The result is 21.3 g of an oily product which crystallizes out slowly. The GC content of 3,4-dichlorobenzoyl cyanide is 85.9%. The yield corresponds to 91.2% of theory.

High-vacuum distillation (boiling point 0.2 mbar/112° C.) produces pure 3,4-dichlorobenzoyl cyanide (GC purity 97%) having a melting point of 70° C. to 71° C.

EXAMPLE 1b

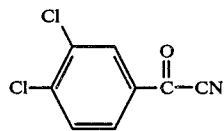

20.2 g (0.1 mole) of cyano-(3,4-dichlorophenyl)-(hydroxy)-methane are introduced at room temperature into 50 ml (81.9 g/0.69 mole) of thionyl chloride. The mixture is stirred at said temperature for 24 hours, the small amount of precipitate which is formed is filtered off with suction, and the reaction product is freed of excess thionyl chloride.

The result is 19.4 g of an oily product. The GC content of 3,4-dichlorobenzoyl cyanide is 51.5%; the yield corresponds to 50.5% of theory.

The product is worked up using high vacuum distillation (113° C. to 114° C./0.3 mbar). The resulting pure 3,4-dichlorobenzoyl cyanide has a melting point of 70° C. to 71° C.

The following compounds of the formula (I) can be obtained analogously to Examples (1a) and (1b):

$$R-\underset{\underset{O}{\|}}{C}-CN \qquad (I)$$

| Example No. | R | Yield (% of theory) | Melting point (°C.) |
|---|---|---|---|
| 2 | 2-Cl-phenyl | 83.2 | 35 |
| 3 | 4-Cl-phenyl | 82.2 | 40–41 |
| 4 | 3,5-Cl$_2$-phenyl | 80.0 | |
| 5 | 3,4,5-Cl$_3$-phenyl | 89.2 | |
| 6 | 2,6-Cl$_2$-phenyl | 40.0 | |
| 7 | 2,4-Cl$_2$-phenyl | 12.5 | |
| 8 | phenyl | 36.4 | 31 |

Comparative example (A):

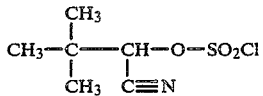

11.3 g (0.1 mole) of cyano-(2,2-dimethyl)-(1-hydroxy)-propane are stirred at 60° C. in 20.2 ml (33.7 g/0.25 mole) of sulphuryl chloride for 6 hours. Excess sulphuryl chloride is removed to leave 20.2 g (95% crude yield) of an oily product. The GC content of cyano-(2,2-dimethyl)-(1-chlorosulphonyl)-propane is 84.4%. Distillation under a water jet vacuum at 98° C. to 99° C./20 mbar produces the product in pure form.

It will be understood that the specification and examples are illustrative but not limitative of the present invention and that other embodiments within the spirit and scope of the invention will suggest themselves to those skilled in the art.

We claim:

1. A process for preparing an α-ketonitrile of the formula

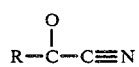

in which R is optionally substituted aryl, comprising reacting a cyanohydrin of the formula

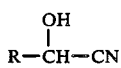

with sulphuryl chloride or thionyl chloride.

2. A process according to claim 1, in which R is phenyl which is optionally monosubstituted to trisubstituted by $C_1$–$C_4$-alkyl, $C_1$–$C_4$-alkoxy, nitro and/or halogen.

3. A process according to claim 1, in which R is phenyl, 2-chlorophenyl, 4-chlorophenyl, 3,4-dichlorophenyl, 3,5-dichlorophenyl, 2,4-dichlorophenyl, 2,6-dichlorophenyl, 4-methoxyphenyl or 3,4,5-trichlorophenyl.

4. A process according to claim 1, wherein the reaction is effected at about 15° to 30° C.

5. A process according to claim 1, wherein the reaction is effected in a diluent.

6. A process according to claim 1, wherein about 1 to 10 moles of sulphuryl chloride or thionyl chloride are employed per mole of cyanohydrin.

7. A process according to claim 1, wherein about 1 to 2.5 moles of sulphuryl chloride or thionyl chloride are employed per mole of cyanohydrin.

8. A process according to claim 3, wherein the reaction is effected at about 15° to 30° C. in a diluent and about 1 to 2.5 moles of sulphuryl chloride or thionyl chloride are emloyed per mole of cyanohydrin.

* * * * *